(12) United States Patent
Ishii et al.

(10) Patent No.: US 10,130,398 B2
(45) Date of Patent: Nov. 20, 2018

(54) VERTEBRAL SURGERY INSTRUMENT

(71) Applicants: KYOCERA Medical Corporation, Osaka-shi, Osaka (JP); Ken Ishii, Tokyo (JP); Morio Matsumoto, Tokyo (JP); Yoshiaki Toyama, Tokyo (JP)

(72) Inventors: Ken Ishii, Tokyo (JP); Morio Matsumoto, Tokyo (JP); Yoshiaki Toyama, Tokyo (JP); Masaki Atarashi, Osaka (JP); Junji Ito, Osaka (JP)

(73) Assignee: KYOCERA CORPORATION, Kyoto-Shi, Kyoto (JP)

( * ) Notice: Subject to any disclaimer, the term of this patent is extended or adjusted under 35 U.S.C. 154(b) by 0 days.

(21) Appl. No.: 15/329,740

(22) PCT Filed: Jun. 29, 2015

(86) PCT No.: PCT/JP2015/068645
§ 371 (c)(1),
(2) Date: Jan. 27, 2017

(87) PCT Pub. No.: WO2016/042877
PCT Pub. Date: Mar. 24, 2016

(65) Prior Publication Data
US 2017/0215928 A1 Aug. 3, 2017

(30) Foreign Application Priority Data
Sep. 18, 2014 (JP) .................................. 2014-189994

(51) Int. Cl.
*A61B 17/70* (2006.01)
*A61B 17/86* (2006.01)
*A61B 17/88* (2006.01)

(52) U.S. Cl.
CPC ...... *A61B 17/7082* (2013.01); *A61B 17/7077* (2013.01); *A61B 17/7086* (2013.01); *A61B 17/86* (2013.01); *A61B 17/8875* (2013.01)

(58) Field of Classification Search
CPC combination set(s) only.
See application file for complete search history.

(56) References Cited

U.S. PATENT DOCUMENTS 7,476,240 B2    1/2009   Raymond et al.
8,137,356 B2    3/2012   Hestad et al.
(Continued)

FOREIGN PATENT DOCUMENTS

JP    2007-520319 A    7/2007
JP    4574931 B2    11/2010
(Continued)

OTHER PUBLICATIONS

International Search Report, PCT/JP2015/068645, dated Sep. 29, 2015, 2 pgs.
(Continued)

*Primary Examiner* — Jan Christopher Merene
(74) *Attorney, Agent, or Firm* — Volpe and Koenig, P.C.

(57) ABSTRACT

A vertebral surgery instrument includes: an engagement part for engaging with a pair of opposing parts provided on or attached to a vertebral implant in a state in which the vertebral implant is fixed to a vertebra, the pair of opposing parts forming a slit into which a fixation rod for fixing a plurality of vertebrae to each other is to be inserted; and a pair of guide parts that are provided integrally with or attached to the engagement part. The pair of guide parts are formed extending so as to separate from each other toward a side on which the fixation rod is to be inserted, in a state in which the engagement part is engaged with the pair of opposing parts, and the slit and a guide passage that is (Continued)

formed between the pair of guide parts are in communication with each other.

8 Claims, 13 Drawing Sheets

(56) References Cited

U.S. PATENT DOCUMENTS

| | | | | |
|---|---|---|---|---|
| 8,317,796 | B2* | 11/2012 | Stihl | A61B 17/7091 |
| | | | | 606/279 |
| 9,173,687 | B2* | 11/2015 | Fowler | A61B 17/7074 |
| 2005/0192589 | A1 | 9/2005 | Raymond et al. | |
| 2006/0074418 | A1* | 4/2006 | Jackson | A61B 17/7086 |
| | | | | 606/914 |
| 2006/0111712 | A1 | 5/2006 | Jackson | |
| 2007/0288026 | A1* | 12/2007 | Shluzas | A61B 17/02 |
| | | | | 606/86 A |
| 2008/0243052 | A1 | 10/2008 | Pond et al. | |
| 2009/0204159 | A1* | 8/2009 | Justis | A61B 17/708 |
| | | | | 606/323 |
| 2009/0216281 | A1 | 8/2009 | Vonwiller et al. | |
| 2010/0168803 | A1* | 7/2010 | Hestad | A61B 17/708 |
| | | | | 606/86 A |
| 2013/0103094 | A1* | 4/2013 | Beale | A61B 17/7076 |
| | | | | 606/279 |
| 2015/0164495 | A1* | 6/2015 | Petit | A61B 17/708 |
| | | | | 600/210 |
| 2015/0164569 | A1* | 6/2015 | Reitblat | A61B 17/7077 |
| | | | | 606/279 |

FOREIGN PATENT DOCUMENTS

| | | |
|---|---|---|
| JP | 2013-111260 A | 6/2013 |
| WO | 01/28436 A1 | 4/2001 |

OTHER PUBLICATIONS

Family List for Japanese Patent Application No. 2003-511190 (Mar. 25, 2003), 5 pgs.

* cited by examiner

VERTEBRAL SURGERY INSTRUMENT

CROSS-REFERENCE TO RELATED APPLICATION

This application is based upon and claims the benefit of priority from Japanese patent application No. 2014-189994, the disclosure of which is herein incorporated by reference in its entirety.

BACKGROUND OF THE INVENTION

1. Field of the Invention

The present invention relates to a vertebral surgery instrument used in a spinal operation.

2. Description of Related Art

Conventionally, vertebral fixation devices are known that are provided with a vertebral implant that holds a fixation rod for fixing a plurality of vertebrae to each other, and an extender for use as a retractor that is attached to the vertebral implant to widen an incision. With such a vertebral fixation device, a plurality of vertebral implants are respectively implanted in the vertebrae, and then the fixation rod is inserted into slits in the implants so as to span the implants. Then, the fixation rod is fixed to the vertebral implants by set screws, and thus the plurality of vertebrae can be fixed to each other. In a spinal operation, of a plurality of vertebrae fixed to each other in the above-described manner, a vertebra that is the target of the surgical operation is subjected to a predetermined treatment.

Also, an instrument disclosed in, for example, Japanese Patent No. 4574931 is known as an instrument for correctly inserting the fixation rod into the slits in the implants. With a pivot arm of this instrument that is swingably fixed to a base end side of an anchor extension (extender), the fixation rod is inserted into the slits formed in a plurality of anchors (vertebral implants) so as to span them.

SUMMARY OF THE INVENTION

However, the instrument disclosed in Japanese Patent No. 4574931 above is a relatively complex mechanism, and a relatively long time is needed to assemble the instrument. Furthermore, because the pivot arm of this instrument swings along a predetermined plane, there are cases where a movable range of the fixation rod is limited, and it is not possible to smoothly insert the fixation rod into the slits in the vertebral implants.

The present invention was made to solve the above-described problems, and the object thereof is to provide a vertebral surgery instrument in which it is easy to insert a fixation rod into slits in vertebral implants, and that has a simple configuration.

(1) In order to achieve the above-described object, a vertebral surgery instrument according to an aspect of the present invention includes: an engagement part for engaging with a pair of opposing parts provided on or attached to a vertebral implant in a state in which the vertebral implant is fixed to a vertebra, the pair of opposing parts forming a slit into which a fixation rod for fixing a plurality of vertebrae to each other is to be inserted; and a pair of guide parts that are provided integrally with or attached to the engagement part, wherein the pair of guide parts are formed extending so as to separate from each other toward a side on which the fixation rod is to be inserted, in a state in which the engagement part is engaged with the pair of opposing parts, and the slit and a guide passage that is formed between the pair of guide parts are in communication with each other.

According to this configuration, when the engagement part is engaged with the pair of opposing parts, the slit and the guide passage that is formed between the pair of guide parts are in communication with each other. In this state, the pair of guide parts are formed extending so as to separate from each other toward a side on which the fixation rod is to be inserted. That is, in this configuration, when the engagement part is engaged with the pair of opposing parts, the pair of guide parts are arranged so as to spread apart toward the side on which the fixation rod is to be inserted. Accordingly, when an operator inserts the front end part of the fixation rod toward the slit, the front end part of the fixation rod will be guided by the pair of guide parts to the slit side, even if the front end part of the fixation rod is inserted slightly shifted with respect to the slit.

Moreover, according to this configuration, it is possible to configure an instrument for inserting the fixation rod into the slit in the vertebral implant with a configuration that includes the engagement part and the pair of guide parts with relatively simple shapes.

Therefore, according to this configuration, it is possible to provide a vertebral surgery instrument in which it is easy to insert a fixation rod into a slit in a vertebral implant, and that has a simple configuration.

(2) Preferably, the engagement part is configured to engage with outer portions of the pair of opposing parts.

In this configuration, the engagement part does not need to be formed so as to engage with inner portions of the pair of opposing parts. Accordingly, a passage width into which the fixation rod is inserted can be secured, and thus it is possible to smoothly insert the fixation rod into the slit.

(3) Preferably, the engagement part is configured to engage with inner portions of the pair of opposing parts.

In this configuration, the engagement part does not need to be formed so as to engage with the outer portions of the pair of opposing parts. Accordingly, it is possible to down-size the outer shape of the portion in the vicinity of the engagement part of the vertebral surgery instrument, and thus it is possible to provide a vertebral surgery instrument that is appropriate for a minimally invasive surgical operation.

(4) Preferably, in the vertebral surgery instrument, an opening is formed in a portion on a side opposite to the vertebral implant fixed to the vertebra, in the state in which the engagement part is engaged with the pair of opposing parts.

In this configuration, a set screw to be screwed into a vertebral implant can be inserted into the vertebral implant via the opening, and thus it is possible to provide a user-friendly vertebral surgery instrument.

(5) More preferably, the vertebral surgery instrument further includes a grip part that extends obliquely to a direction in which the opening is open.

In this configuration, when the vertebral surgery instrument is used, it is possible to prevent the grip part, which is a part to be held by an operator, from interfering with an instrument (such as a driver) for screwing the above-described set screw into the vertebral implant. Accordingly, it is possible to provide a more user-friendly vertebral surgery instrument.

(6) Preferably, the pair of guide parts are tapered toward the vertebral implant in the state in which the engagement part is engaged with the pair of opposing parts.

According to this configuration, the tapered parts, on the front end side, of the pair of guide parts are inserted into a retracted portion of a patient, and thus it is possible to provide a vertebral surgery instrument that is appropriate for a minimally invasive surgical operation.

(7) Preferably, the vertebral surgery instrument further includes a cap part for externally covering end portions of the pair of opposing parts that are on a side opposite to the vertebral implant so as to restrict the pair of opposing parts from approaching each other or separating from each other.

According to this configuration, because the cap part restricts the pair of opposing parts from approaching each other or separating from each other, it is possible to reduce the risk of the pair of opposing parts breaking, which may be caused by the pair of opposing parts approaching each other or separating from each other.

(8) More preferably, the cap part is provided as the engagement part.

According to this configuration, because the above-described cap part functions as the engagement part, the formation of an engagement part in another portion of the vertebral surgery instrument can be omitted. As a result, it is possible to downsize the vertebral surgery instrument.

DETAILED DESCRIPTION OF THE INVENTION

Figure 1:
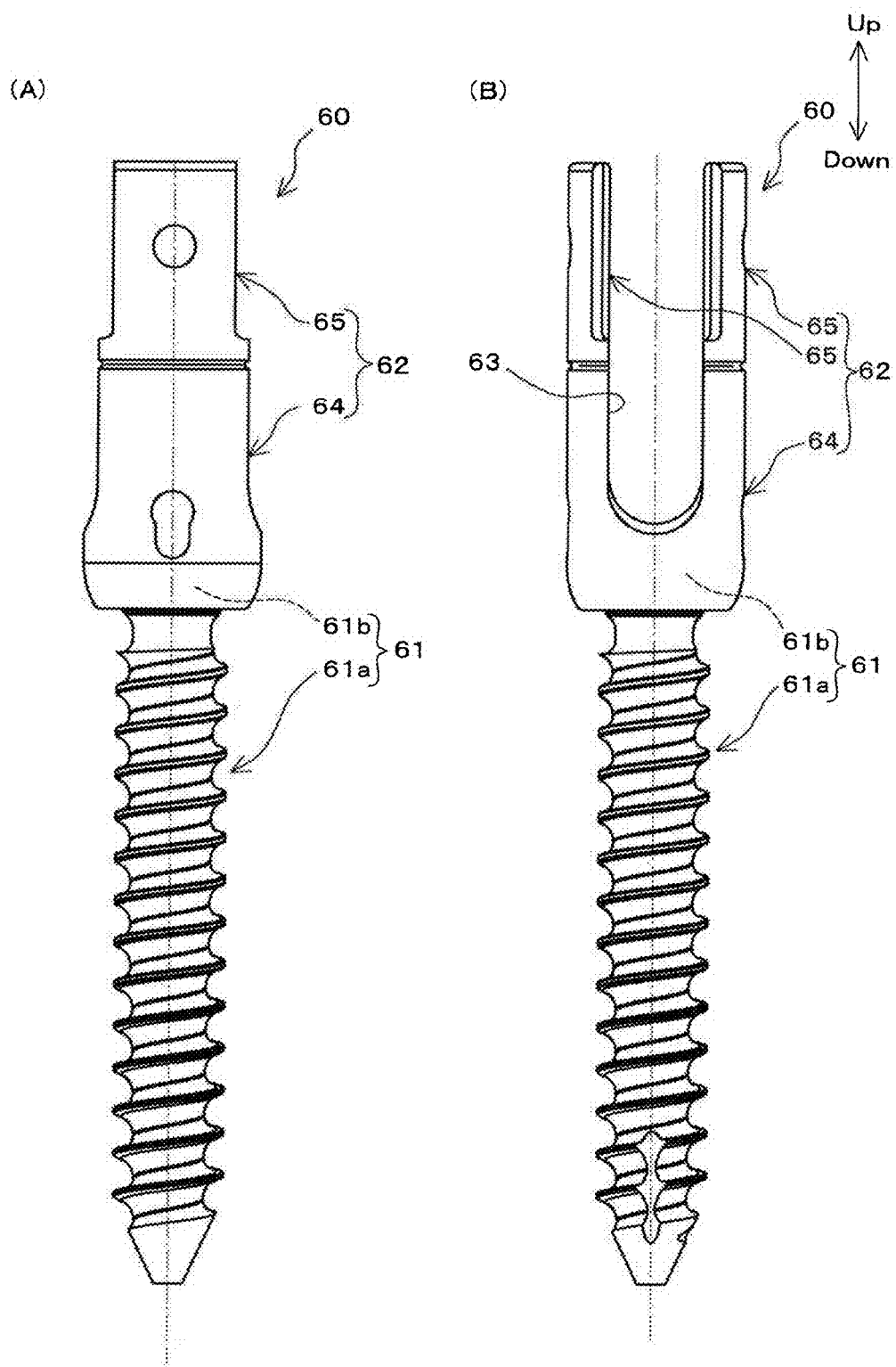
FIG. 1A and FIG. 1B illustrate a shape of a reduction screw of a vertebral fixation device, with FIG. 1A being a front view and FIG. 1B being a side view.

Hereinafter, an embodiment for implementing the present invention will be described with reference to the drawings. Note that the following will first describe a configuration of an example of a vertebral fixation device 50 for which a rod catcher 1 (vertebral surgery instrument) according to the embodiment of the present invention is used, and then a configuration of the rod catcher 1 according to the present embodiment.

Configuration of Vertebral Fixation Device

The vertebral fixation device 50 is used for performing a treatment called reduction. "Reduction" is a treatment that is performed on a patient with spondylolisthesis to put a vertebra that has shifted forward of the body of the patient relative to the other vertebrae back to its original position (to the back side).

As an example, the vertebral fixation device 50 is provided with a reduction screw 60, a standard screw 70, an extender 80, and the like. The reduction screw 60 and the standard screw 70 are used as vertebral implants for fixing a fixation rod 51 to vertebrae, the fixation rod 51 being for fixing adjacent vertebrae to each other. The extender 80 functions as a retractor for widening an incision into which the set screw 52 used to fix the fixation rod 51 to the reduction screw 60 is to be inserted.

Configurations of Reduction Screw and Standard Screw

Figure 2:
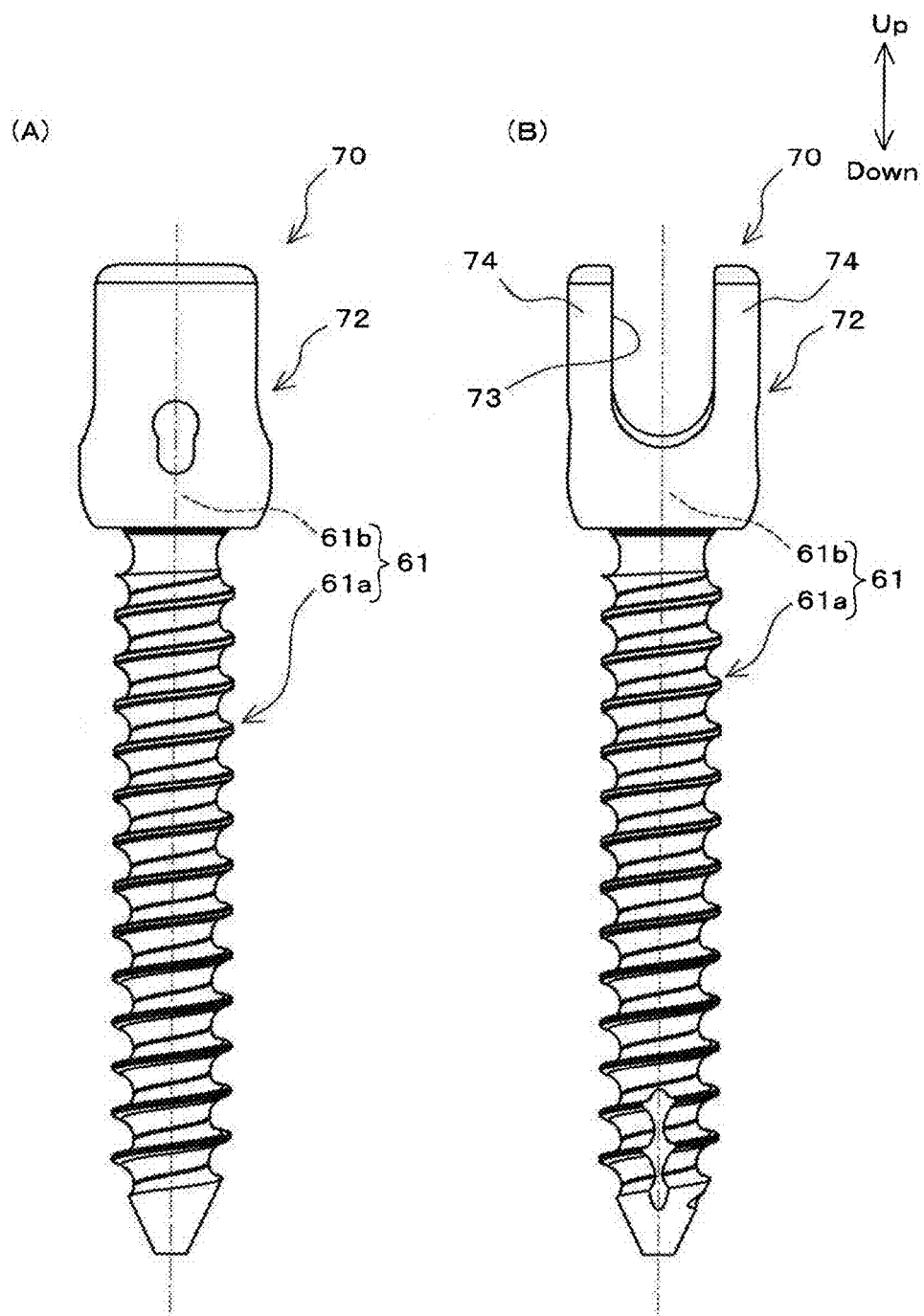
FIG. 2A and FIG. 2B illustrate a shape of a standard screw, with FIG. 2A being a front view and FIG. 2B being a side view.

FIG. 1A and FIG. 1B show a front view and a side view of the reduction screw 60, and FIG. 2A and FIG. 2B show a front view and a side view of the standard screw 70. As shown in FIG. 1A, FIG. 1B, FIG. 2A, and FIG. 2B, the screws 60 and 70 are provided with a screw part 61 and a head part 62 or 72. Note that in the drawings, for convenience of illustration, the direction indicated by the "up" arrows is referred to as "upper side" or "upward", the direction indicated by the "down" arrows is referred to as "lower side" or "downward", the direction indicated by the "right" arrows is referred to as "right side", the direction indicated by the "left" arrows is referred to as "left side", the direction indicated by the "front" arrows is referred to as "front side", and the direction indicated by the "rear" arrows is referred to as "rear side".

The screw parts 61 of the screws 60 and 70 have the same configuration. The screw part 61 includes a screw body part 61a and a screw head part 61b, which are integrally formed. The screw part 61 is a substantially rod-shaped member that extends in an up-down direction, and the screw body part 61a is threaded on its outer circumferential surface.

The head parts 62 and 72 are substantially tubular members in which two slits 63 and 73 are formed, and are formed so as to extend upward from the upper portion of the screw part 61. A female thread into which the set screw 52 is to be screwed is formed on the inner circumference of the head parts 62 and 72. A through hole (not shown) is formed in the lower end portions of the head parts 62 and 72.

In the screws 60 and 70, the screw body part 61a extends downward through the through hole in a state in which the screw head part 61b of the screw part 61 is accommodated in the head parts 62 and 72. The lower side (screw body part 61a side) portion of the screw head part 61b is held so as to be rotatable with respect to the rim portion of the through hole. Accordingly, the head parts 62 and 72, and the screw part 61 are rotatable relative to each other.

The reduction screw 60 and the standard screw 70 have different configurations as per the following points. Specifically, the head part 62 of the reduction screw 60 is formed so as to have a length in the tube axis direction that is longer than that of the standard screw 70. Furthermore, the slit 63 in the reduction screw 60 is formed so as to have a length in the tube axis direction that is longer than that of the slit 73 in the standard screw 70.

The head part 62 of the reduction screw 60 includes a base part 64 and a pair of tab parts 65, which are integrally formed. The base part 64 is a portion, on the screw part 61 side, of the head part 62. The pair of tab parts 65 are shaped as pieces that extend upward from the base part 64, and the slit 63 is formed therebetween. The pair of tab parts 65 are configured to be able to respectively engage with lower end portions of blades 81 of the extender 80, which will be described in detail later.

On the other hand, the standard screw 70 includes, in the upper portion of the head part 72, a pair of opposing parts 74 that extend upward from the lower portion of the head part 72 so as to oppose each other.

Configuration of Extender

As described above, the extender 80 is used as a retractor for widening an incision into which the set screw 52 used to fix the fixation rod 51 to the reduction screw 60 is to be inserted. Furthermore, with the extender 80, it is also possible to secure the visibility of an area that has been cut open through the incision.

FIG. 3A and FIG. 3B illustrate the extender 80 in a state of being engaged with the reduction screw 60, with FIG. 3A being a front view and FIG. 3B being a side view. The extender 80 is constituted by two blades 81. Each blade 81 is an elongated member that is almost arc-shaped in its transverse cross section. The lower end portions of the blades 81 are configured to be able to engage with the tab parts 65 of the reduction screw 60. The space between the pair of blades 81 serves as a slit 82.

Configuration of Rod Catcher

Figure 4:
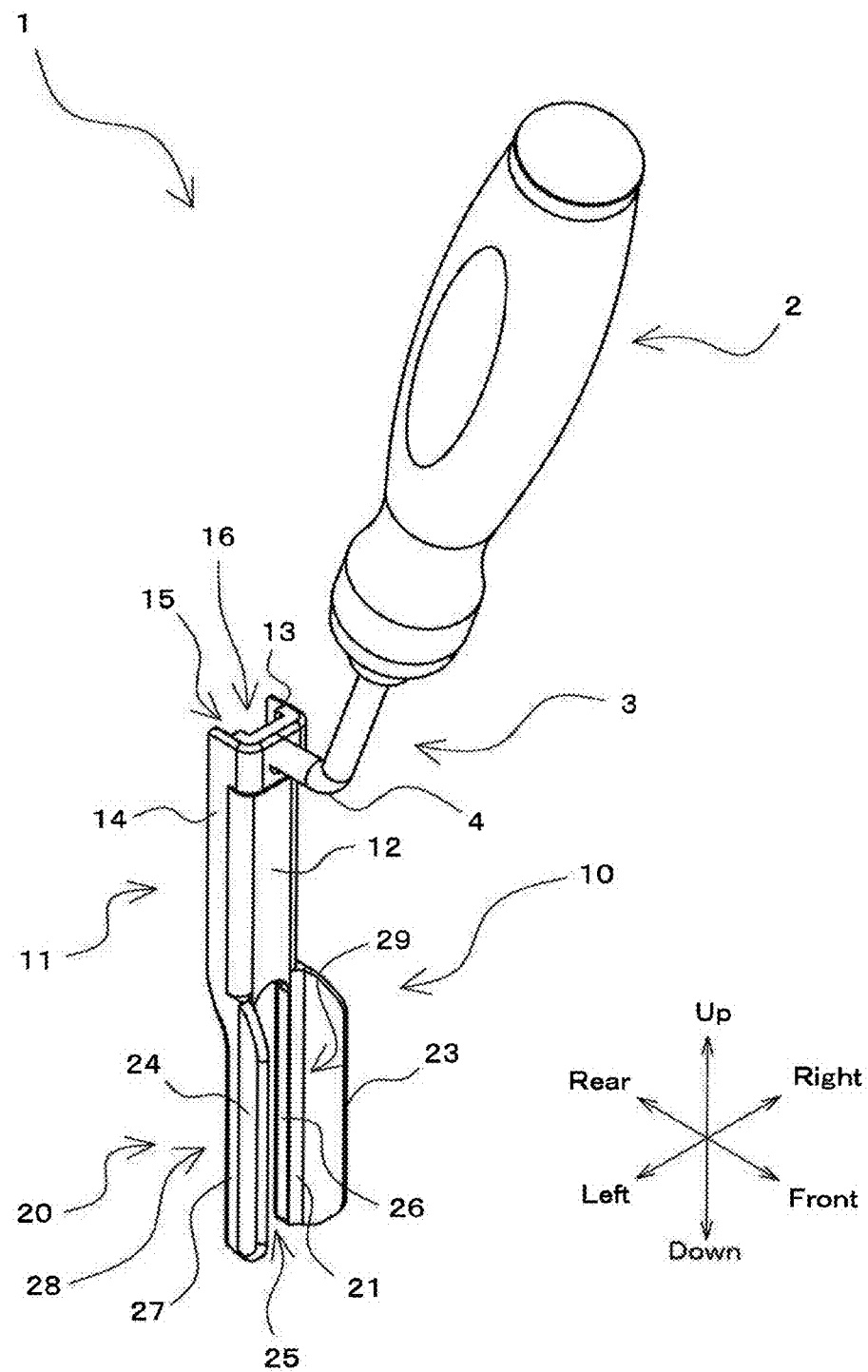
FIG. 4 is a perspective view of a rod catcher according to the present embodiment.
Figure 5:
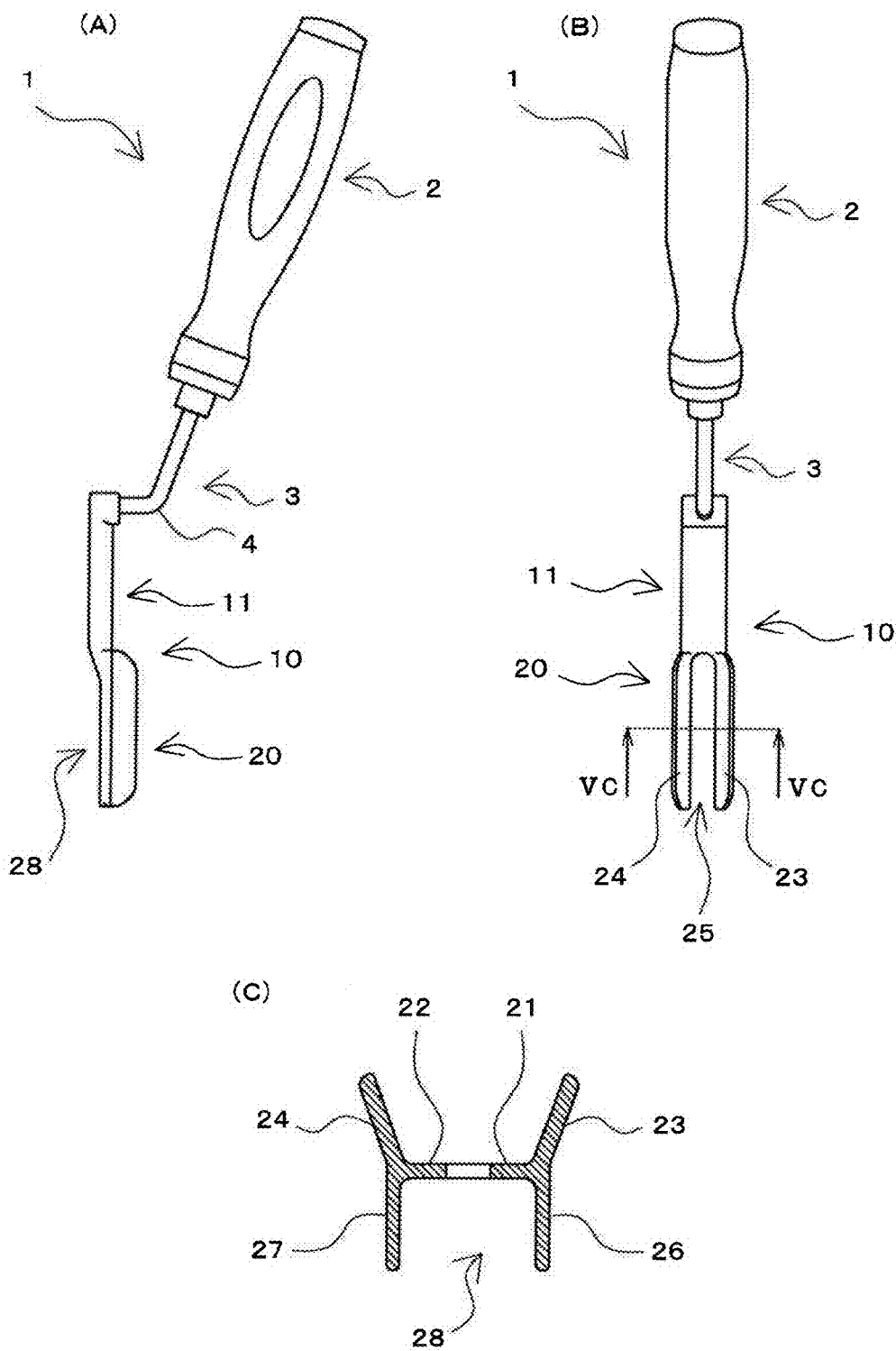
FIG. 5A, FIG. 5B, and FIG. 5C illustrate the rod catcher shown in FIG. 4, with FIG. 5A being a diagram viewed from a lateral side, FIG. 5B being a diagram viewed from a front side, and FIG. 5C being a cross-sectional view taken along a line VC-VC of FIG. 5B.

The following will describe a configuration of the rod catcher 1 according to the present embodiment. FIG. 4 is a perspective view of the rod catcher 1. Furthermore, FIG. 5A, FIG. 5B, and FIG. 5C illustrate the rod catcher 1 shown in FIG. 4, with FIG. 5A being a diagram viewed from a lateral side, FIG. 5B being a diagram viewed from the front side, and FIG. 5C being a cross-sectional view taken along a line VC-VC of FIG. 5B.

The rod catcher 1 is an instrument that is used to insert the fixation rod 51 into the slit 63 of the reduction screw 60 fixed to a vertebra. In a minimally invasive surgical operation, an affected area is cut open so that the range of a cut in a human body is small, and thus a retracted portion (incision) into which the fixation rod is to be inserted is not cut open over a wide range. Accordingly, an operator cannot sufficiently visually check the portion into which the fixation rod is to be inserted, and thus it is difficult for the operator to insert the fixation rod 51 into the slit 63. In contrast, with the use of the rod catcher 1 according to the embodiment, it is possible to easily insert the fixation rod into the slit 63, which will be described in detail later.

The rod catcher 1 includes a body part 10, a grip part 2, and a coupling part 3.

The body part 10 is formed of a metal member that extends in the up-down direction. The body part 10 includes a base end part 11 that serves as an upper portion (portion on the grip part 2 side) of the body part 10, and a front end part 20 that serves as a lower portion (portion on the side opposite to the grip part 2) of the body part 10, which are integrally formed.

The base end part 11 includes a front face part 12, a right face part 13, and a left face part 14, which are integrally formed. These face parts 12, 13, and 14 are provided as plate-shaped parts that are elongated in the up-down direction. The right face part 13 is provided so as to protrude rearward from the right-side edge of the front face part 12. On the other hand, the left face part 14 is provided so as to protrude rearward from the left-side edge of the front face part 12.

Figure 3:
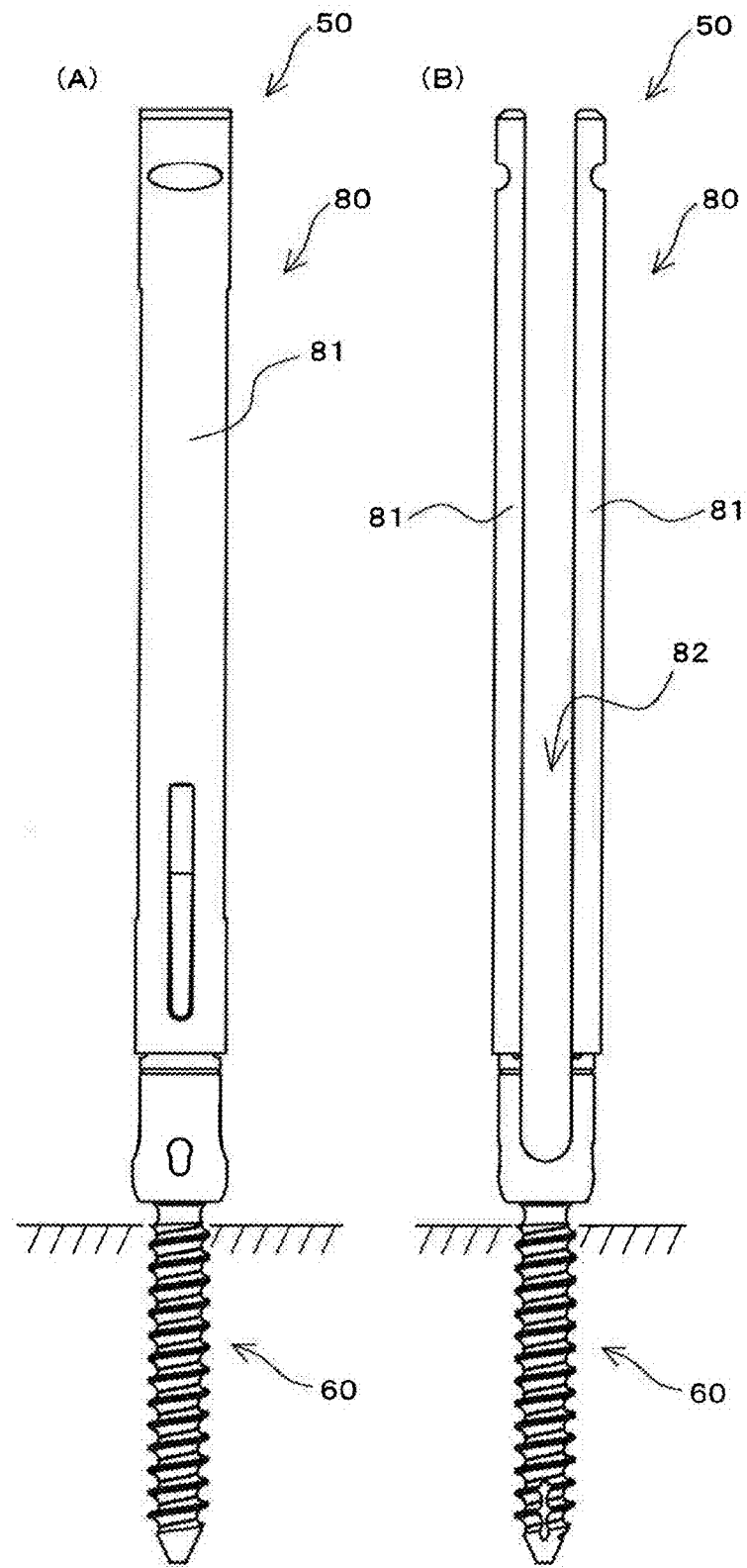
FIG. 3A and FIG. 3B illustrate an extender in a state of being engaged with the reduction screw, with FIG. 3A being a front view and FIG. 3B being a side view.

Also, the rear-side part of the above-described base end part 11 is provided as a first engagement part 15 that engages with the extender 80 serving as a pair of opposing parts that are engaged with the reduction screw 60 as shown in FIG. 3, so as to sandwich the extender 80 from the outside. The first engagement part 15 engages with the upper portion of the extender 80. Accordingly, the rod catcher 1 can engage with the extender 80. Furthermore, the upper portion of the above-described base end part 11 is provided with an opening 16 that is open upward.

The front end part 20 includes a right extension part 21, a left extension part 22, a right guide part 23, and a left guide part 24.

The right extension part 21 is formed so as to extend downward from the front side portion on the lower side of the right face part 13. Similarly, the left extension part 22 is formed so as to extend downward from the front side portion on the lower side of the left face part 14. Accordingly, a slit part 25 in the shape of a slit whose lower side is open is formed between the right extension part 21 and the left extension part 22.

The right-side edge of the right extension part 21 is provided with a right wall part 26 that protrudes rearward from this part. The right wall part 26 is formed so as to extend from the upper portion to the lower portion of the right extension part 21.

Similarly, the left-side edge of the left extension part 22 is provided with a left wall part 27 that protrudes rearward from this part. The left wall part 27 is formed so as to extend from the upper portion to the lower portion of the left extension part 22.

Also, the rear side part of the above-described front end part 20 is provided as a second engagement part 28 that engages with the extender 80 serving as the pair of opposing parts that are engaged with the reduction screw 60 as shown in FIG. 3, so as to sandwich the extender 80 from the outside. The second engagement part 28 engages with the lower portion of the extender 80. Accordingly, it is possible to engage the rod catcher 1 with the extender 80.

The right guide part 23 and the left guide part 24 are provided as a pair of guide parts 23 and 24. The right guide part 23 and left guide part 24 are respectively formed integrally with the right extension part 21 and the left extension part 22. The guide parts 23 and 24 are respectively formed at the front side portions of the extension parts 21 and 22, spanning the upper end portions and the lower end portions of the extension parts 21 and 22.

Also, the pair of guide parts 23 and 24 are formed so as to gradually separate from each other toward the front side from the rear side. In other words, a gap between the pair of guide parts 23 and 24 gradually increases from the rear side toward the front side. The gap formed in the above-described manner between the pair of guide parts 23 and 24 functions as a guide passage 29 for guiding the fixation rod 51 to the slit 63 in the reduction screw 60, which will be described in detail later.

The grip part 2 is provided as a part that is held by an operator during an operation. The grip part 2 is coupled to the body part 10 via the coupling part 3, which will be described in detail later. The grip part 2 is provided so as to extend, from a portion that is located upward and slightly forward relative to the body part 10, upward and obliquely to a direction (up-down direction) in which the body part 10 extends. In other words, the grip part 2 extends upward and obliquely to a direction (direction along the up-down direction) in which the opening 16 formed in the body part 10 is open. Accordingly, the upper side of the opening 16 is not covered by the grip part 2.

The coupling part 3 is a rod-shaped part that is partially provided with a bent part 4, and has one end that is connected to the upper end portion of the front face part 12 of the body part 10, and the other end that is connected to the grip part 2. Accordingly, the coupling part 3 couples the body part 10 to the grip part 2.

Engagement of Rod Catcher with Reduction Screw and Extender

Figure 6:
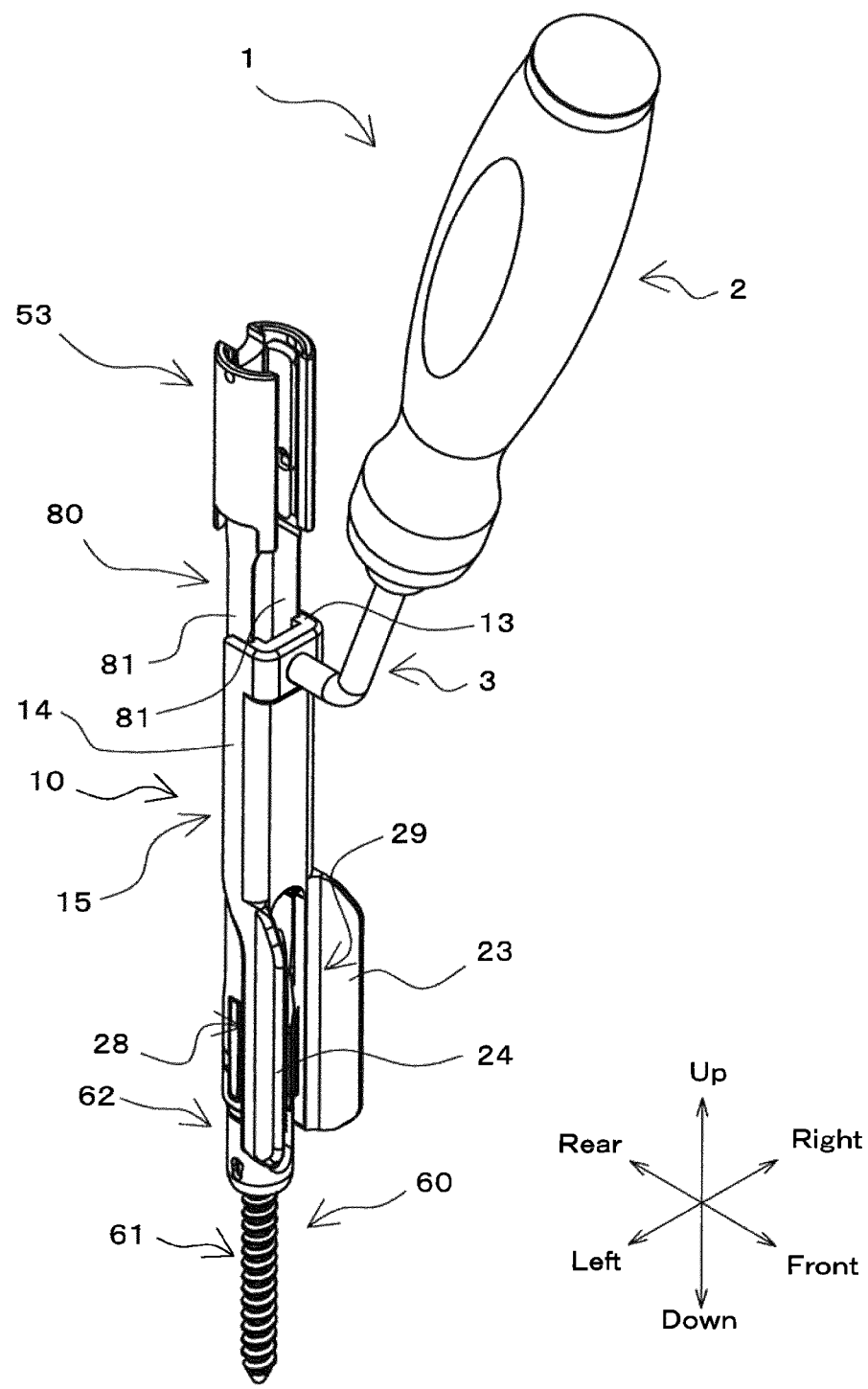
FIG. 6 is a perspective view of the rod catcher that is engaged with the reduction screw and the extender.
Figure 7:
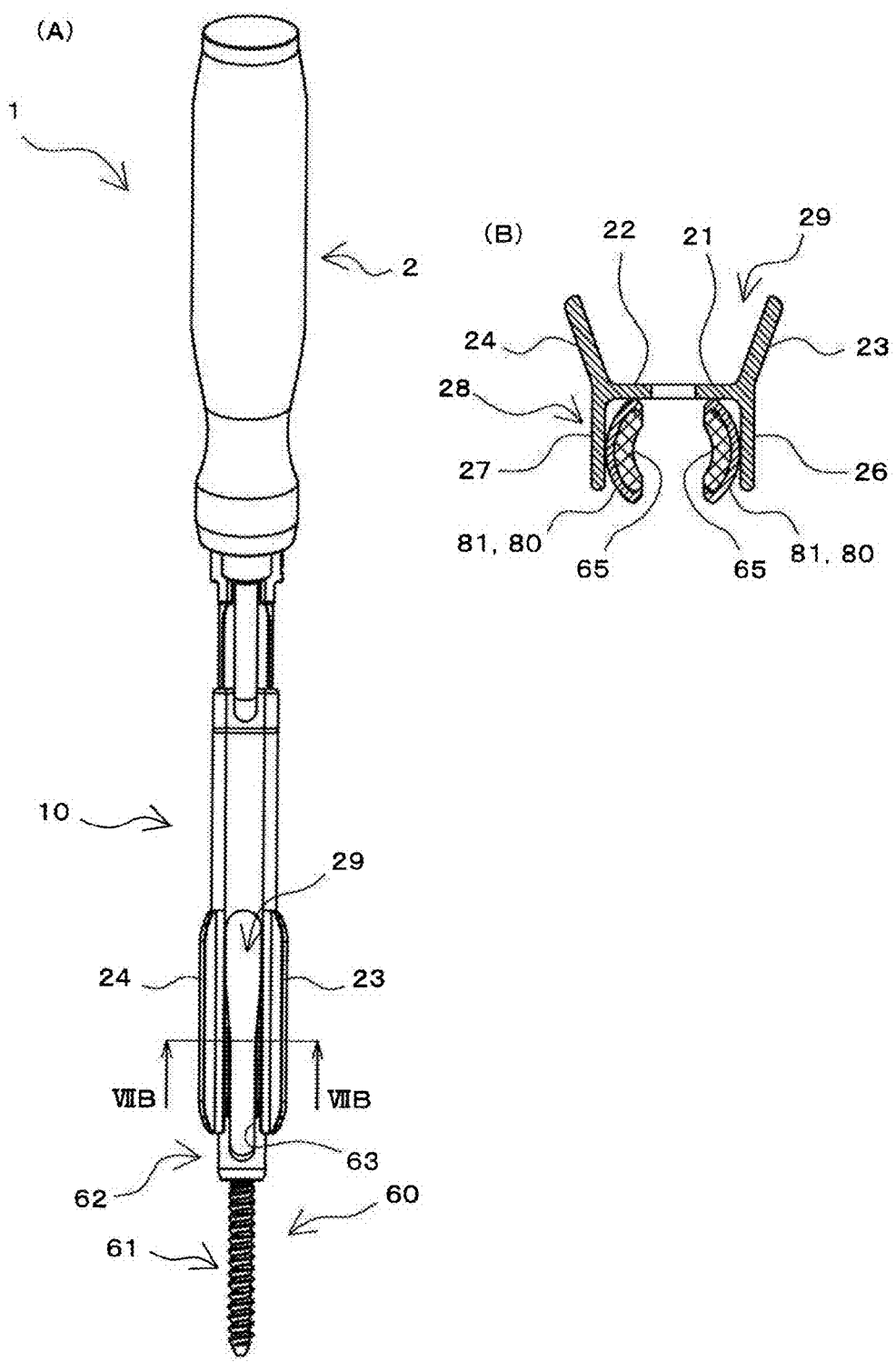
FIG. 7A is a diagram, viewed from the front side, of the rod catcher in the state shown in FIG. 6.
FIG. 7B is a cross-sectional view taken along a line VIIB-VIIB of FIG. 7A.

FIG. 6 is a perspective view of the rod catcher 1 that is engaged with the reduction screw 60 and the extender 80. Furthermore, FIG. 7A is a diagram, viewed from the front side, of the rod catcher 1 in the state shown in FIG. 6, and FIG. 7B is a cross-sectional view taken along a line VIIB-VIIB of FIG. 7A. Note that, before the extender 80 is engaged with the rod catcher 1, a substantially tubular cap 53 is attached to the extender 80 so as to restrict the pair of blades 81 of the extender 80 from approaching each other or separating from each other.

As shown in FIGS. 6, 7A, and 7B, the rod catcher 1 engages with the extender 80 that is engaged with the reduction screw 60. The first engagement part 15 of the rod catcher 1 engages with the upper portion of the extender 80, and the second engagement part 28 engages with the lower portion of the extender 80. Specifically, as a result of the extender 80 being sandwiched by the pair of face parts 13 and 14 (the right face part 13 and the left face part 14) of the first engagement part 15 from the outside, the first engagement part 15 and the extender 80 are engaged with each other. Furthermore, as a result of the lower portion of the extender 80 being sandwiched by the pair of wall parts 26 and 27 (the right wall part 26 and the left wall part 27) of the second engagement part 28 from the outside, the second engagement part 28 and the extender 80 are engaged with each other. Accordingly, it is possible to position the rod catcher 1 in a left-right direction with respect to the extender 80.

Also, as described above, in the state in which the rod catcher 1 is positioned with respect to the extender 80, the gap (that is, the guide passage 29) between the pair of guide parts 23 and 24 of the rod catcher 1 and the slit 63 formed between the pair of tab parts 65 are in communication with each other from the front side to the rear side.

Procedure of Reduction

Figure 8:
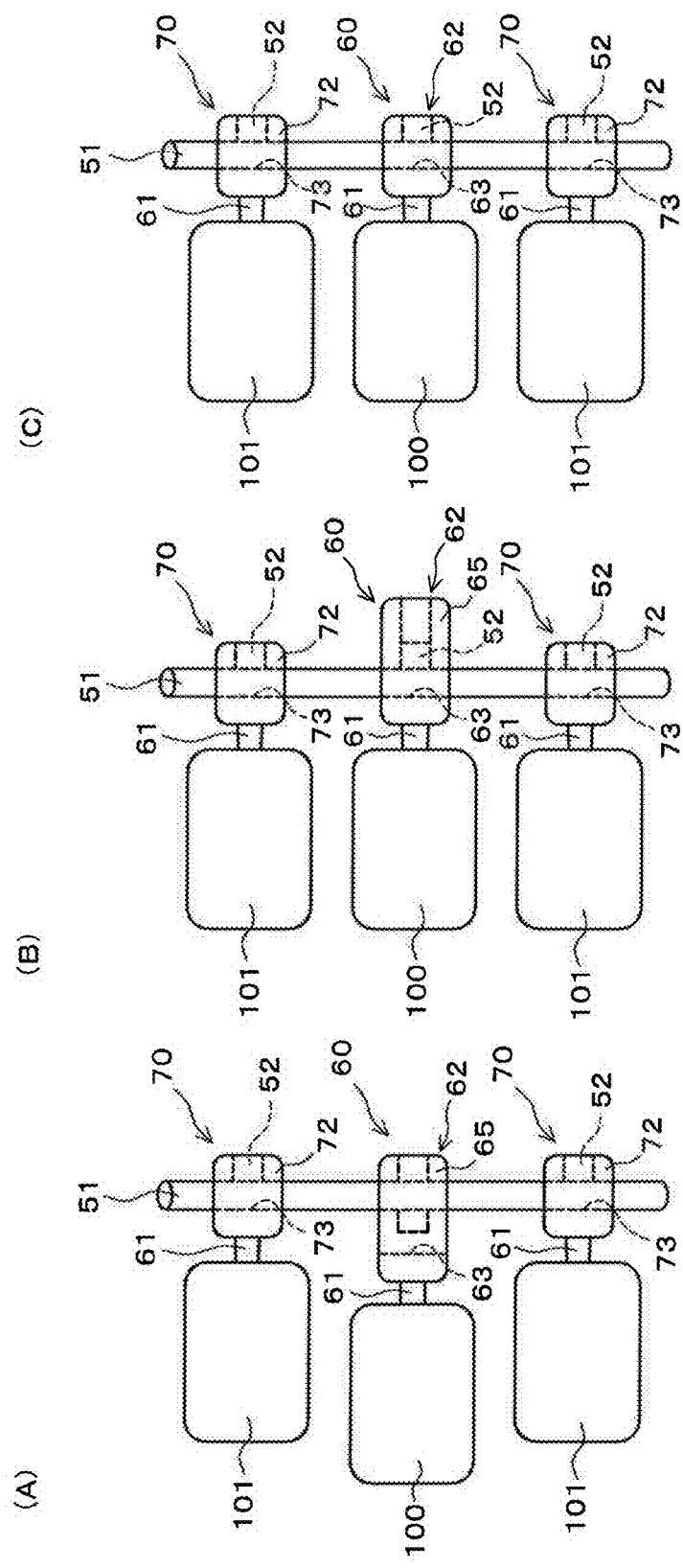
FIG. 8A, FIG. 8B, and FIG. 8C schematically illustrate an operation that is performed when reduction is performed using the reduction screw shown in FIG. 1, with FIG. 8A being a diagram before reduction is performed, FIG. 8B being a diagram after reduction is performed, and FIG. 8C being a diagram illustrating a state in which tab parts of the reduction screw are separated after reduction is performed.

FIG. 8A and FIG. 8B schematically illustrate an operation that is performed when reduction is performed using the reduction screw 60 according to the present embodiment, with FIG. 8A being a diagram showing a state before reduction is performed, and FIG. 8B being a diagram showing a state after reduction is performed. The procedure when reduction is performed is described with reference to FIG. 8A and FIG. 8B. Three vertebrae shown in FIG. 8A and FIG. 8B are an affected area of a patient with spondylolis-thesis, and includes a vertebra 100 that has shifted forward of the body of the patient, and two vertebrae 101 that are adjacent to the vertebra 100. The vertebra 100 is a vertebra that is the target for reduction.

First, an operator makes an incision in the back or the like of the patient, and then the reduction screw 60 and the standard screws 70 are implanted by being screwed into the vertebrae 100 and 101. Specifically, the operator implants the standard screws 70 into the vertebrae 101, and implants the reduction screw 60 into the vertebra 100. Note that the extender 80 is engaged with the reduction screw 60 that is implanted into the vertebra 100, but the illustration of the extender 80 is omitted in FIG. 8A, and FIG. 8B.

Then, the operator inserts the fixation rod 51 into the slits 63 and 73 formed in the screws 60 and 70. At this time, the operator can easily insert the fixation rod 51 into the slit 63 using the rod catcher 1 according to the present embodiment. A specific usage of the rod catcher 1 will be described later.

Then, the operator screws the set screws 52 into the head parts 72 of the standard screws 70. Accordingly, the fixation rod 51 is held by being sandwiched between the head parts 72 and the set screws 52, and thus the fixation rod 51 is fixed between the two vertebrae 101 (see FIG. 8A). Note that at this time, as shown in FIG. 8A, the fixation rod 51 is positioned at a portion on the front end side of the slit 63 of the reduction screw 60 (portion of the slit 63 on the opposite side to the screw part 61).

The reduction is performed in the above-described state. Specifically, the operator sets the set screw 52 at the front end part (portion of the head part 62 on the opposite side to the screw part 61) of the head part 62 of the reduction screw 60, and screws in the set screw 52. Accordingly, the vertebra 100, together with the reduction screw 60, is pulled to the fixation rod 51 side (see FIG. 8B). Accordingly, it is possible to pull the vertebra 100 to the back side and move it to a desired position.

Note that the tab parts 65 of the reduction screw 60 according to the present embodiment are broken off and removed after the reduction is performed as described above (see FIG. 8(C)) by the operator applying an external force to the blades 81 of the extender 80. Accordingly, the portion of the head part 62 of the reduction screw 60 that protruded above the standard screw 70 is eliminated, and thus it is possible to reduce the parts that remain in the body.

Usage of Rod Catcher

The operator uses the rod catcher 1 according to the present embodiment to insert the fixation rod 51 into the slit 63 of the reduction screw 60 in a manner as described below.

Description is given with reference to FIGS. 4 to 7B, and the like. First, the operator inserts the front end side of the body part 10 of the rod catcher 1 into a retracted portion of the patient. At this time, for example, the operator inserts the rod catcher 1 into the retracted portion in a state in which the first engagement part 15 of the rod catcher 1 is engaged with the upper portion of the extender 80, and inserts the body part 10 into the body until the second engagement part 28 engages with the lower portion of the extender 80. Accordingly, it is possible to easily engage the rod catcher 1 with the extender 80.

Figure 9:
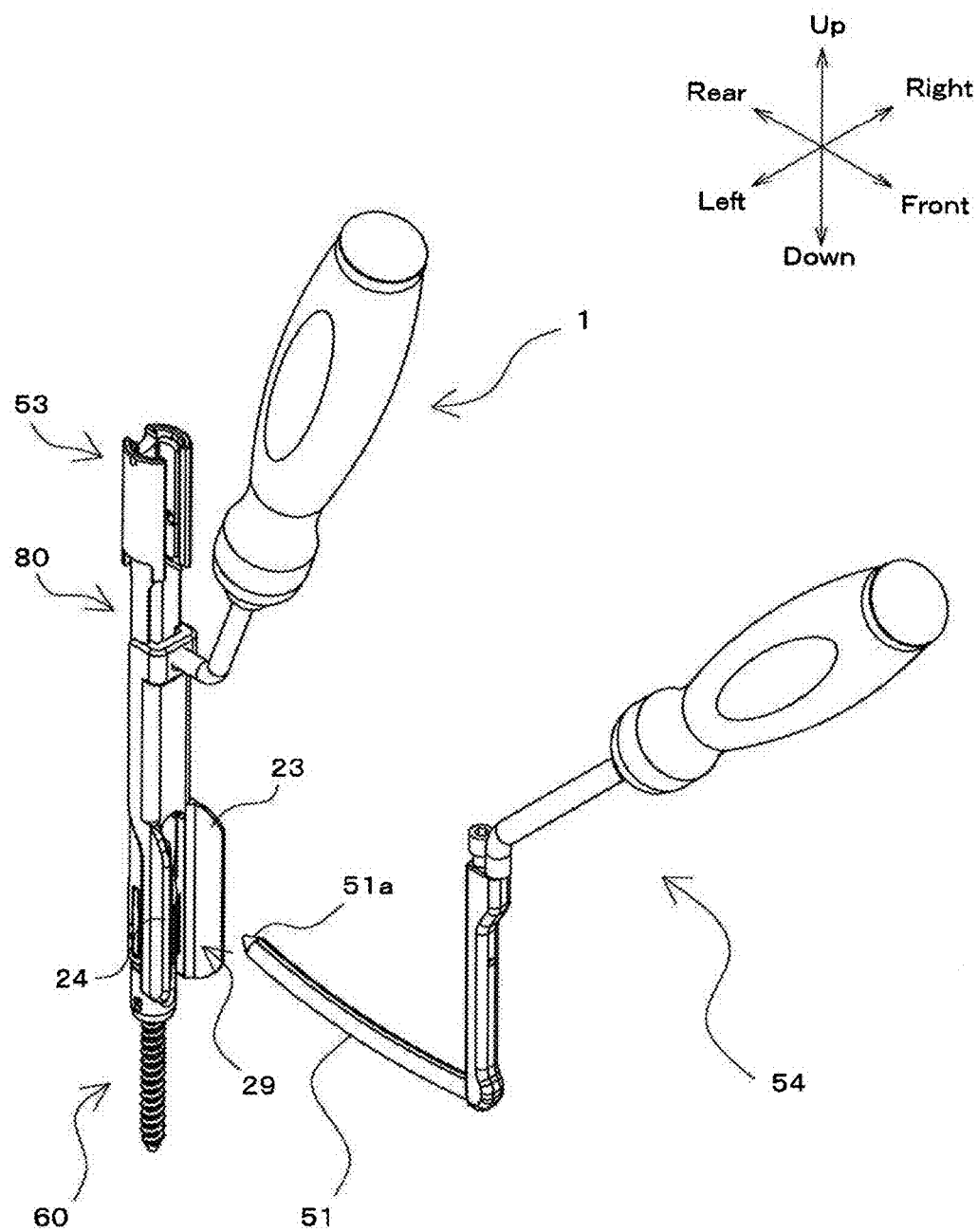
FIG. 9 is a perspective view illustrating a state in which the rod catcher and a rod inserter are used to insert a fixation rod into a slit in the reduction screw.

Then, the operator uses a rod inserter 54 shown in FIG. 9 to insert the fixation rod 51 into the slit 63 of the reduction screw 60. Specifically, the operator inserts a front end part 51a of the fixation rod 51 fixed to the rod inserter 54 toward the pair of guide parts 23 and 24 from the front side of the rod catcher 1 via the retracted portion of the patient (see FIG. 9).

Ordinarily, in the case of a minimally invasive surgical operation, an affected area is cut open so that the range of a cut in a human body is small, and thus a retracted portion into which the fixation rod 51 is to be inserted is not cut open over a wide range. Accordingly, the operator cannot sufficiently visually check the portion into which the fixation rod 51 is to be inserted, and thus it is difficult for the operator to insert the fixation rod 51 into the slit 63.

In contrast, with the use of the rod catcher 1 according to the present embodiment, the pair of guide parts 23 and 24 that are formed on the side of the rod catcher 1 on which the fixation rod 51 is inserted are formed so as to gradually separate from each other toward the side (front side) on which the fixation rod 51 is to be inserted. In other words, the pair of guide parts 23 and 24 are formed so as to guide the fixation rod 51 to the slit 63. Accordingly, even if the operator inserts the front end part 51a of the fixation rod 51 toward the pair of guide parts 23 and 24 while the front end part 51a being shifted in the left-right direction, the front end part 51a will abut against an inner wall part of either of the pair of guide parts 23 and 24, and will be guided along the wall part into the slit 63. Accordingly, the operator can smoothly insert the fixation rod 51 into the slit 63. Also, the operator can smoothly insert the fixation rod 51 into all of the screws 60 and 70 by repeating the same operation on the remaining reduction screws 60 and standard screws 70 into which the fixation rod 51 is to be inserted.

Effects

As described above, when the first engagement part 15 and the second engagement part 28 of the rod catcher 1 according to the present embodiment are engaged with the extender 80, the guide passage 29 and the slit 63 are in communication with each other. In this state, the pair of guide parts 23 and 24 are formed extending so as to separate from each other toward the side (front side) on which the fixation rod 51 is to be inserted. In other words, when the engagement parts 15 and 28 of the rod catcher 1 are engaged with the extender 80, the pair of guide parts 23 and 24 are arranged so as to spread apart toward the side on which the fixation rod 51 is to be inserted. Accordingly, when the operator inserts the front end part 51a of the fixation rod 51 toward the slit 63, the front end part 51a of the fixation rod 51 will be guided by the pair of guide parts 23 and 24 to the slit 63 side, even if the front end part 51a of the fixation rod 51 is inserted slightly shifted with respect to the slit 63 in the left-right direction.

Moreover, according to the rod catcher 1, it is possible to configure an instrument for inserting the fixation rod 51 into the slit 63 in the reduction screw 60 with a configuration that includes the engagement parts 15 and 28, the pair of guide parts 23 and 24, and the like with relatively simple shapes.

Therefore, with the rod catcher 1, it is possible to provide a vertebral surgery instrument in which it is easy to insert the fixation rod 51 into the slit 63 of the reduction screw 60, and that has a simple configuration.

Furthermore, in the rod catcher 1, the first engagement part 15 and the second engagement part 28 are engaged with the outer portions of the extender 80. With this, the engagement parts do not need to be formed so as to engage with the inner portions of the extender 80. Accordingly, a passage width into which the fixation rod 51 is inserted can be secured, and thus it is possible to smoothly insert the fixation rod 51 into the slit 63.

Furthermore, in the rod catcher 1, the set screw 52 that is to be screwed into the reduction screw 60 can be inserted into the reduction screw 60 side via the opening 16 formed in the rod catcher 1, and thus it is possible to provide a user-friendly vertebral surgery instrument.

Furthermore, the grip part 2 of the rod catcher 1 extends obliquely to the direction in which the opening 16 is open. With this, when the rod catcher 1 is used, it is possible to prevent the grip part 2, which is a part to be held by an operator, from interfering with an instrument such as a driver for screwing the set screw 52 into the reduction screw 60. Accordingly, it is possible to provide a more user-friendly vertebral surgery instrument.

The embodiment of the present invention has been described so far, but the present invention is not limited to the foregoing embodiment, and various modifications are possible without departing from the scope of the description in the claims. For example, the following modifications may be implemented.

Figure 10:
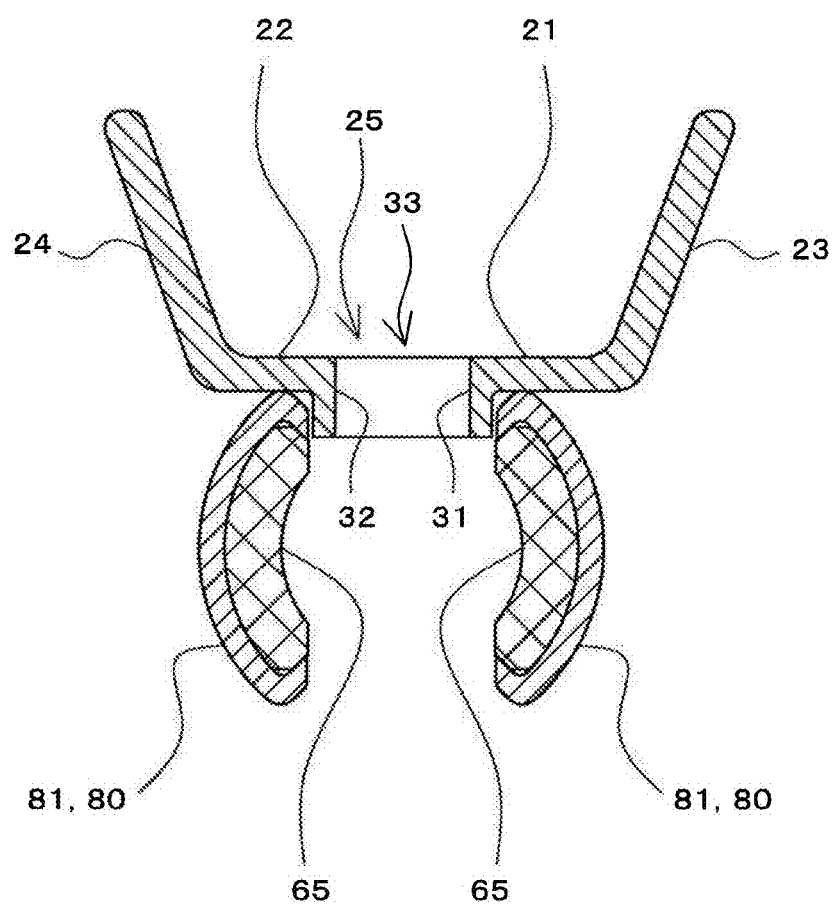
FIG. 10 is a transverse cross-sectional view illustrating a state in which a rod catcher according to a modification is engaged with the reduction screw and the extender, the transverse cross-sectional view corresponding to FIG. 7B.

Modifications (1) FIG. 10 is a transverse cross-sectional view showing a state in which a rod catcher according to a modification is engaged with the reduction screw 60 and the extender 80, the transverse cross-sectional view corresponding to FIG. 7B. In the foregoing embodiment, as shown in FIG. 7B, the rod catcher 1 is engaged with the extender 80 as a result of the lower portion of the extender 80 being sandwiched by the pair of wall parts 26 and 27 from the outside, but the present invention is not limited to this. Specifically, as shown in FIG. 10, the rod catcher may be engaged with the extender 80 as a result of a pair of wall parts 31 and 32 formed at the lower end of the slit part 25 fitting to the inside of the pair of blades 81 of the extender 80. In this case, the above-described pair of wall parts 31 and 32 constitute an engagement part 33 for engaging the rod catcher with the extender 80. Accordingly, it is possible to make the portion of the rod catcher on the front end side smaller than that of the foregoing embodiment, and thus it is possible to provide a vertebral surgery instrument that is appropriate for a minimally invasive surgical operation.

Figure 11:
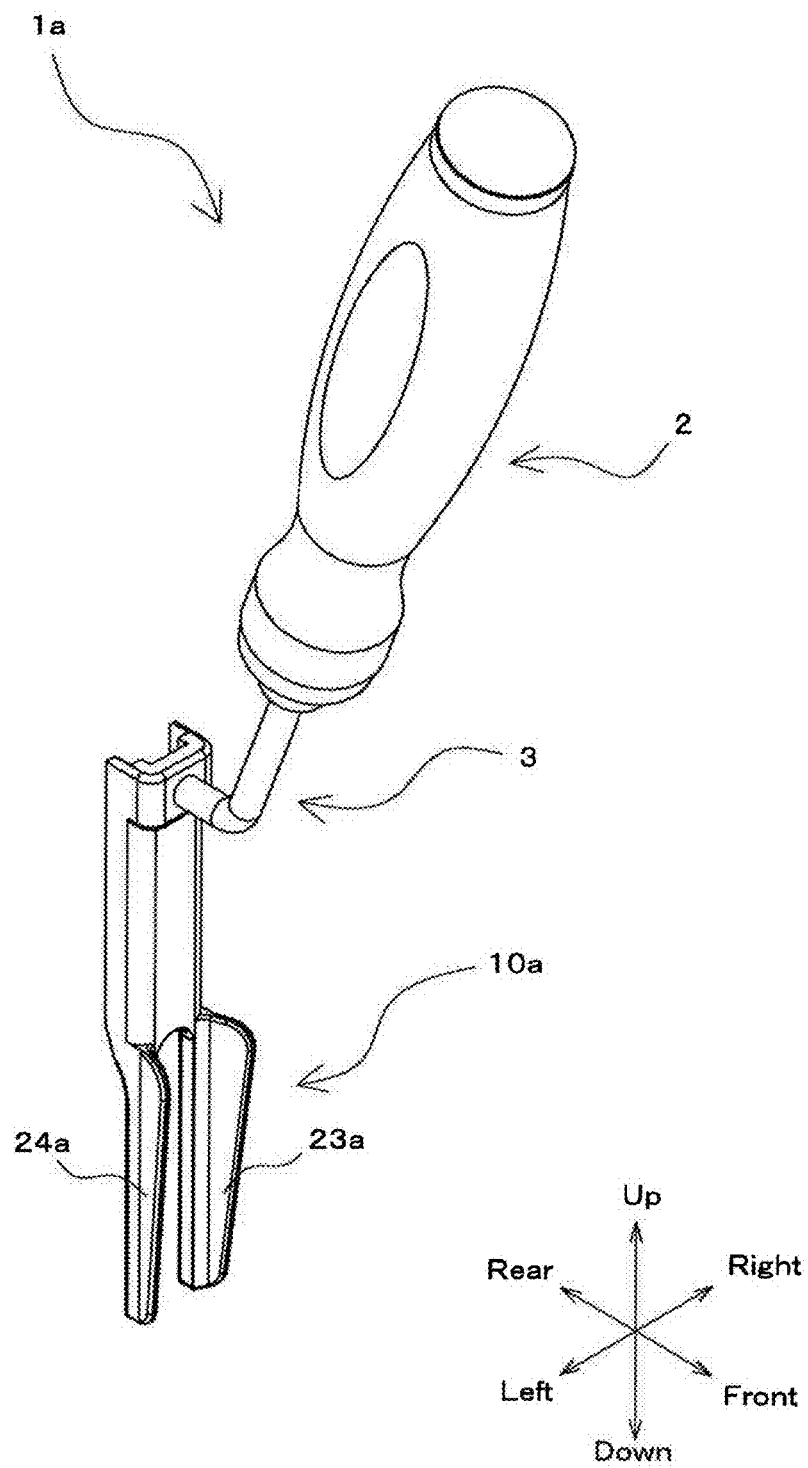
FIG. 11 is a perspective view of the rod catcher according to a modification.

(2) FIG. 11 is a perspective view of a rod catcher 1a according to a modification. The pair of guide parts 23 and 24 of the foregoing embodiment are formed so as to have a constant height from the upper side to the lower side, but the present invention is not limited to this. Specifically, in the rod catcher 1a according to the present modification, guide parts 23a and 24a are formed so that their height gradually decreases from the upper side toward the lower side. In other words, the guide parts 23a and 24a are tapered toward the lower side. Accordingly, it is possible to smoothly insert the pair of guide parts 23a and 24a into a retracted portion, and thus it is possible to provide a vertebral surgery instrument that is appropriate for a minimally invasive surgical operation.

Figure 12:
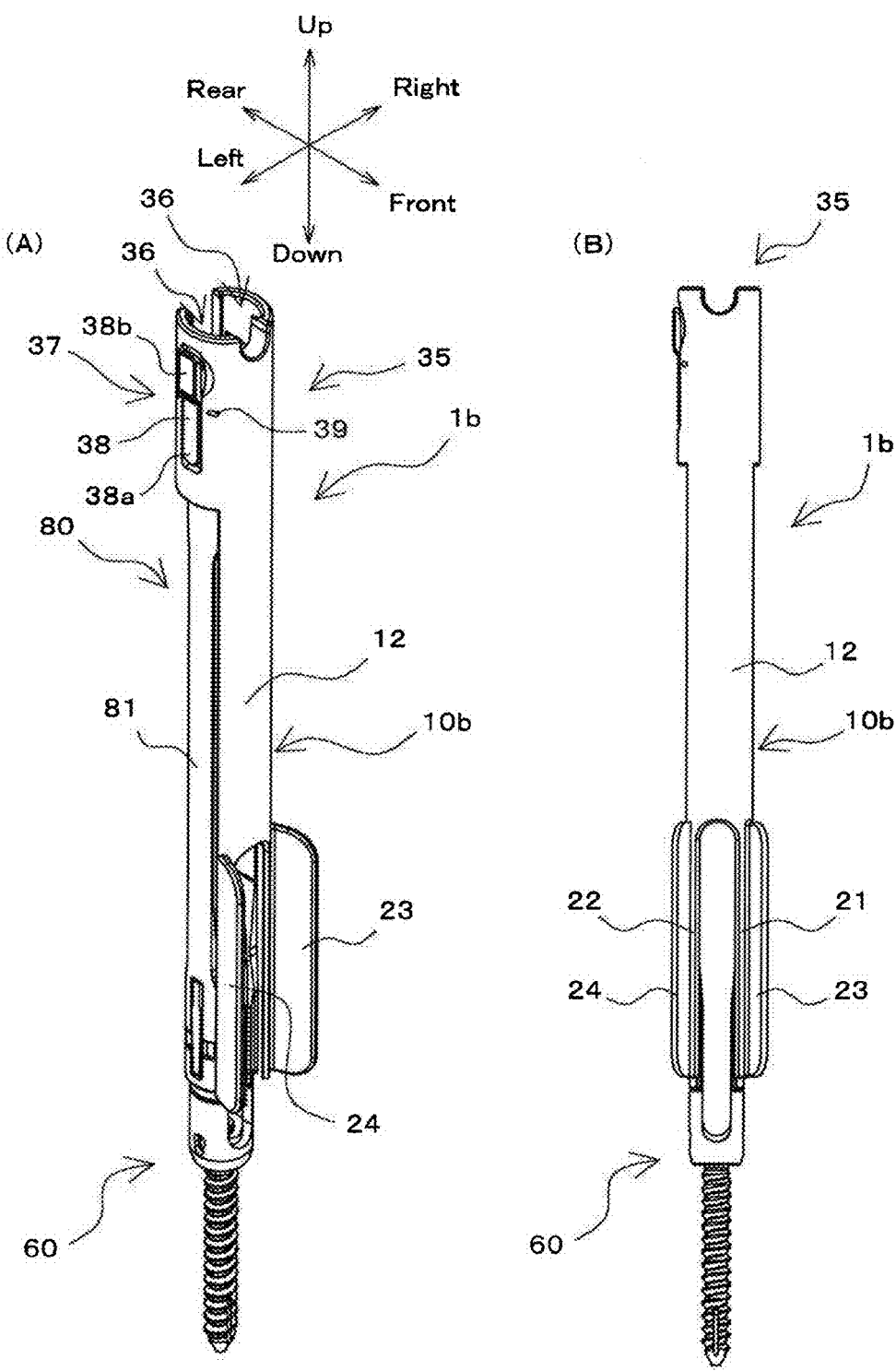
FIG. 12A and FIG. 12B illustrate a rod catcher according to a modification in a state in which it is engaged with the reduction screw and the extender, with FIG. 12A being a perspective view and FIG. 12B being a diagram viewed from the front side.

(3) FIG. 12 is a perspective view of a rod catcher 1b according to a modification, showing a state in which the rod catcher 1b is engaged with the reduction screw 60 and the extender 80. Compared to the rod catcher 1 according to the foregoing embodiment, the rod catcher 1b according to the present modification has a configuration in which the grip part 2 and the coupling part 3 are omitted. Furthermore, the configuration of the rod catcher 1b according to the present modification is such that a cap part 35 is formed integrally with a body part 10b, which has a slightly different configuration from the body part of the foregoing embodiment.

As described above, the rod catcher 1b according to the present modification includes the body part 10b and the cap part 35, which are integrally formed.

The body part 10b includes the front face part 12, the right extension part 21, the left extension part 22, the right guide part 23, and the left guide part 24, which are integrally formed. These parts 12, 21, 22, 23, and 24 have approximately the same shapes as those of the corresponding parts 12, 21, 22, 23, and 24 of the body part 10 of the rod catcher 1 according to the foregoing embodiment.

Specifically, the front face part 12 is provided as an elongated plate-shaped part that is located on the front side of the body part 10b and extends in the up-down direction. The right extension part 21 is formed so as to extend downward from the right side portion at the lower end portion of the front face part 12, and the left extension part 22 is formed so as to extend downward from the left side portion at the lower end portion of the front face part 12. The right guide part 23 and the left guide part 24 respectively extend to the front side from the right extension part 21 and the left extension part 22 so as to separate from each other. Note that the rod catcher 1b according to the present modification does not include an engagement part that has a shape corresponding to the first engagement part 15 and the second engagement part 28 of the rod catcher 1 according to the foregoing embodiment.

As shown in FIG. 12, the cap part 35 is a substantially tubular part that is provided extending upward from the upper end portion of the body part 10b. The cap part 35 is provided with a pair of notch grooves 36 that are formed in the inner side of the cap part 35 in the shape of a groove extending in the up-down direction, and the blades 81 of the extender 80 are respectively engaged with the notch grooves 36. Accordingly, the pair of blades 81 are restricted from approaching each other or separating from each other.

Furthermore, the cap part 35 is provided with a positioning part 37 for positioning the rod catcher 1b with respect to the extender 80 in the up-down direction. The positioning part 37 includes a piece part 38 that has the shape of a piece elongated in the up-down direction, and that is provided so as to penetrate the cap part 35 in the thickness direction, as shown in FIG. 12. The piece part 38 is swingable using a support shaft 39 that is provided in the central portion in the up-down direction of the piece part 38 as a supporting point.

The piece part 38 is provided with, in an inner portion of a front end part 38a, a protrusion part (not shown) that protrudes to the inside of the cap part 35, and is fitted into a hole (or a recess) formed in the blade 81 so as to engage therewith. Accordingly, it is possible to position the rod catcher 1b in the up-down direction. Note that in order to disengage the above-described protrusion part from the hole of the blade 81, it is sufficient to press a base end part 38b of the piece part 38 to oppose a biasing force of a torsion spring (not shown) for biasing the front end part 38a of the piece part 38 to the inside of the cap part 35. With this, the protrusion part formed in the front end part 38a of the piece part 38 is separated from the hole of the blade 81, and thus the positioning of the rod catcher 1b with respect to the extender 80 in the up-down direction is solved.

Furthermore, as a result of the cap part 35 being attached to the extender 80 in the above-described manner, the rod catcher 1b is engaged with the extender 80. In other words, the cap part 35 of the present modification is provided as an engagement part for engaging the rod catcher 1b with the pair of blades 81 serving as a pair of opposing parts.

As described above, because the cap part 35 restricts the pair of blades 81 from approaching each other or separating from each other, the rod catcher 1b according to the present modification can reduce the risk of the pair of blades 81 breaking, which may be caused by the pair of blades 81 approaching each other or separating from each other.

Furthermore, in the rod catcher 1b, because the cap part 35 functions as an engagement part for engaging the rod catcher 1b with the extender 80, it is possible to eliminate the formation of an engagement part in another portion of the rod catcher 1b. As a result, it is possible to downsize the rod catcher 1b.

Figure 13:
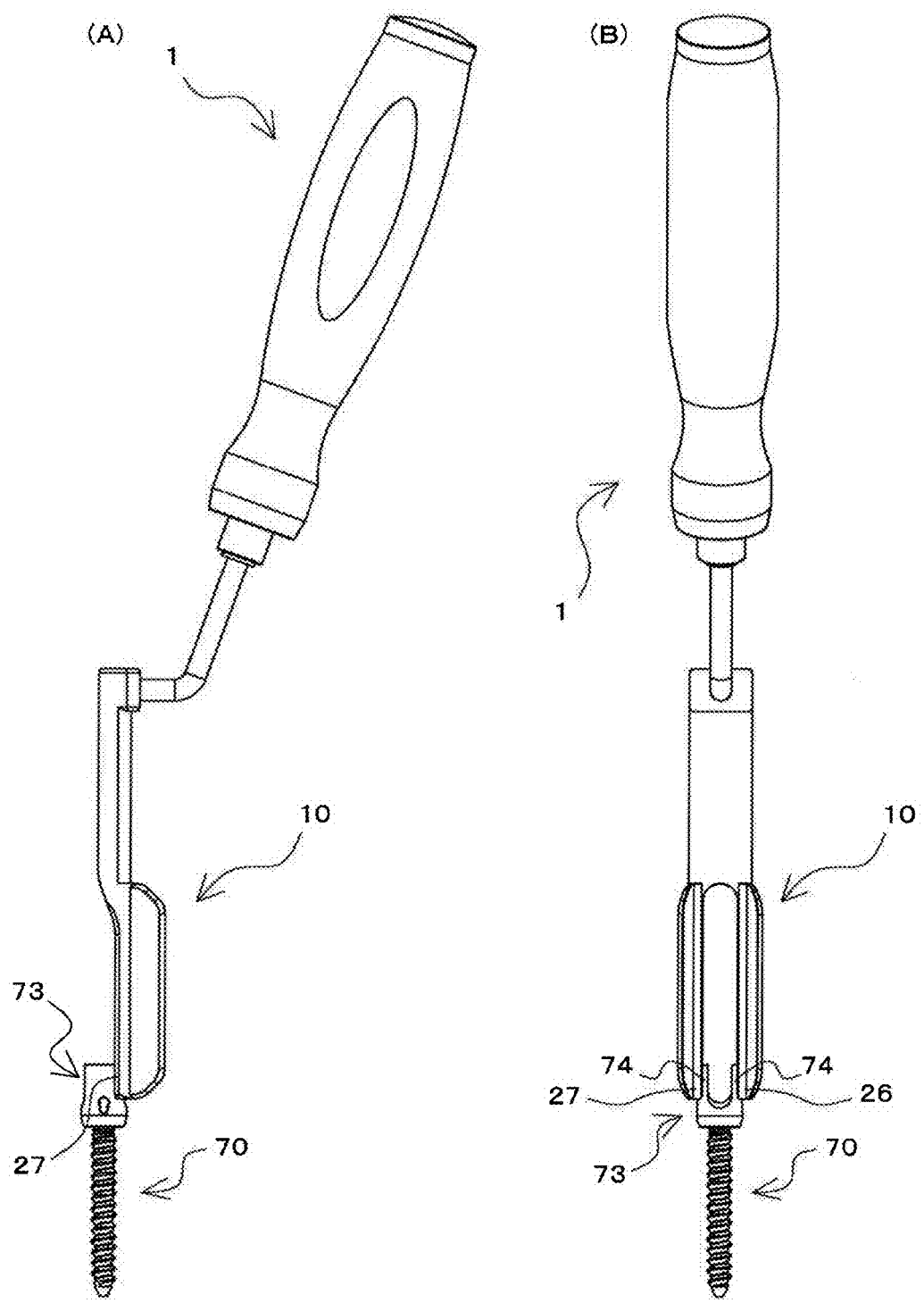
FIG. 13A and FIG. 13B illustrate a state in which the rod catcher shown in FIG. 4 is engaged with the standard screw, with FIG. 13A being a diagram viewed from a lateral side and FIG. 13B being a diagram viewed from the front side.

(4) FIG. 13A and FIG. 13B illustrate a state in which the rod catcher 1 according to the foregoing embodiment is engaged with the standard screw 70, with FIG. 13A being a diagram viewed from a lateral side and FIG. 13B being a diagram viewed from the front side. The description above was made taking an example in which the rod catcher 1 is applied to the reduction screw 60 and the extender 80 that is attached to the reduction screw 60, but the present invention is not limited to this. Specifically, the rod catcher 1 may also be applied to the standard screw 70, as shown in FIG. 13A and FIG. 13B.

In order to apply the rod catcher 1 to the standard screw 70 as shown in FIG. 13A and FIG. 13B, it is sufficient to set the rod catcher 1 with respect to the standard screw 70 such that the pair of opposing parts 74 of the standard screw 70 are sandwiched by the pair of wall parts 26 and 27 (the right wall part 26 and the left wall part 27) formed in the body part 10 of the rod catcher 1 from the outside. In this way, it is possible to apply the rod catcher 1 having the above-described configuration to not only the reduction screw 60 but also the standard screw 70.

(5) The foregoing embodiment and modifications have been described taking examples in which the rod catcher 1 is applied to the reduction screw 60 and the standard screw 70, but the present invention is not limited to these. Specifically, the rod catcher 1 may be applied to a vertebral implant of another shape as long as it is a vertebral implant including a pair of opposing parts that form a slit into which the fixation rod is to be inserted.

The present invention is widely applicable as a vertebral surgery instrument for inserting a fixation rod into a slit in a vertebral implant.

The invention claimed is:

1. A vertebral surgery instrument comprising:
   a body part comprising:
      an engagement portion having a first engagement part and a second engagement part, the engagement portion configured to engage with a pair of opposing parts attached to a vertebral implant in a state in which the vertebral implant is fixed to a vertebra, the pair of opposing parts forming a slit into which a fixation rod for fixing a plurality of vertebrae to each other is to be inserted; and
   a pair of guide parts that are provided integrally with or attached to the engagement portion and extend in an up-down direction,
   wherein the first engagement part is provided on an upper portion of the body part and is configured to engage an upper portion of the pair of opposing parts, and the second engagement part is provided on a lower portion of the body part and is configured to engage a lower portion of the pair of opposing parts,
   wherein each of the pair of guide parts are formed in a plate shape extending a first distance from an outer surface of the engagement portion in a rear-front direction perpendicular to the up-down direction and extending a second distance, in a left right direction perpendicular to the up-down direction and the rear-front direction, less than the first distance, the pair of guide parts extending so as to separate from each other toward a side on which the fixation rod is to be inserted, in a state in which the engagement portion is engaged with the pair of opposing parts, and the slit and a guide passage that is formed between the pair of guide parts are in communication with each other, and the second engagement part is provided at a location which corresponds to the pair of guide parts in the up-down direction.

2. The vertebral surgery instrument according to claim 1, wherein the engagement portion is configured to engage with outer portions of the pair of opposing parts.

3. The vertebral surgery instrument according to claim 1, wherein the engagement portion is configured to engage with inner portions of the pair of opposing parts.

4. The vertebral surgery instrument according to claim 1, wherein an opening is formed in a portion on a side opposite to the vertebral implant fixed to the vertebra, in the state in which the engagement portion is engaged with the pair of opposing parts.

5. The vertebral surgery instrument according to claim 4, further comprising:
a grip part that extends obliquely to a direction in which the opening is open.

6. The vertebral surgery instrument according to claim 1, wherein the pair of guide parts are tapered toward the vertebral implant in the state in which the engagement portion is engaged with the pair of opposing parts.

7. The vertebral surgery instrument according to claim 1, further comprising:
a cap part for externally covering end portions of the pair of opposing parts that are on a side opposite to the vertebral implant so as to restrict the pair of opposing parts from approaching each other or separating from each other.

8. The vertebral surgery instrument according to claim 7, wherein the cap part is provided as the first engagement part.

* * * * *